United States Patent
Janssen et al.

(10) Patent No.: US 6,805,963 B2
(45) Date of Patent: Oct. 19, 2004

(54) ELASTOMERIC ARTICLES WITH IMPROVED DAMP SLIP

(75) Inventors: Robert A. Janssen, Alpharetta, GA (US); Kermit R. Littleton, Ellijay, GA (US); Thomas Gregory Triebes, Alpharetta, GA (US); Mary E. Kister, Cumming, GA (US); Shantilal H. Modha, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 9 days.

(21) Appl. No.: 10/318,343

(22) Filed: Dec. 12, 2002

(65) Prior Publication Data

US 2004/0115444 A1 Jun. 17, 2004

(51) Int. Cl.[7] ............................................. B32B 09/04
(52) U.S. Cl. .................. 428/447; 428/421; 428/495; 428/517; 428/521; 428/451; 2/159; 2/161.7; 2/167; 2/168; 264/319; 264/331.13; 264/331.14; 264/331.15
(58) Field of Search ................................. 428/421, 422, 428/492, 493, 495, 500, 515, 517, 521, 409, 447, 451; 525/359.4, 387; 264/319, 331.13, 331.14, 331.15; 427/384, 385.5, 2.1, 133, 314, 312.2, 372.2, 387; 2/159, 161.7, 167, 168

(56) References Cited

U.S. PATENT DOCUMENTS

| | | | |
|---|---|---|---|
| 3,905,823 A | 9/1975 | Piskoti | |
| 4,061,709 A | 12/1977 | Miller et al. | |
| 4,373,519 A | 2/1983 | Errede et al. | |
| 4,595,632 A | 6/1986 | Mayhan et al. | |
| 5,112,900 A | 5/1992 | Buddenhagen et al. | |
| 5,405,666 A | 4/1995 | Brindle | |
| 5,407,715 A | 4/1995 | Buddenhagen et al. | |
| 5,521,273 A | 5/1996 | Yilgör et al. | |
| 5,545,451 A | 8/1996 | Haung et al. | |
| 5,570,475 A | 11/1996 | Nile et al. | |
| 5,578,598 A | 11/1996 | Abe et al. | |
| 5,601,870 A | 2/1997 | Haung et al. | |
| 5,612,083 A | 3/1997 | Haung et al. | |
| 5,742,943 A | 4/1998 | Chen | |
| 5,792,531 A | 8/1998 | Littleton et al. | |
| 5,872,173 A | 2/1999 | Anand | |
| 5,932,299 A | 8/1999 | Katoot | |
| 5,962,620 A | 10/1999 | Reich et al. | |
| 5,993,972 A | 11/1999 | Reich et al. | |
| 6,221,944 B1 | 4/2001 | Liebeskind et al. | |
| 6,242,041 B1 | 6/2001 | Katoot et al. | |
| 6,284,856 B1 | 9/2001 | Lee | |
| 6,306,514 B1 | 10/2001 | Weikel et al. | |

FOREIGN PATENT DOCUMENTS

| | | |
|---|---|---|
| EP | 0521605 A2 | 1/1993 |
| WO | WO 9625279 A1 | 8/1996 |
| WO | WO 9821270 A1 | 5/1998 |
| WO | WO 9858796 A1 | 12/1998 |
| WO | WO 0174917 A1 | 10/2001 |
| WO | WO 0222721 A2 | 3/2002 |

OTHER PUBLICATIONS

PCT Search Report, Dec. 30, 2003.
Abstract of Japanese Patent No. 02530096 B2, Sep. 4, 1996.
Material Safety Data Sheet for Dow Corning(R) 8600 Hydrophilic Softener from Dow Corning Corporation, 7 pages.

Primary Examiner—David J. Buttner
Assistant Examiner—Christopher Keehan
(74) Attorney, Agent, or Firm—Dority & Manning, P.A.

(57) ABSTRACT

Disclosed is an elastomeric article, such as an elastomeric glove, for example, and a method for making the disclosed elastomeric article. The elastomeric article includes a fluorocarbon graft on the donning surface of the article. In addition, a hydrophilic lubricant including a modified siloxane displaying polar functionality may be applied to the surface of the article. In one embodiment, the modified siloxane may be an amino modified siloxane. The silicone lubricant and the fluorocarbon graft display a synergy, providing an article with improved dry slip characteristics and improved wet slip characteristics. In addition, a fatty alcohol may be applied to the surface of the article, further improving the damp slip characteristics of the article.

41 Claims, 4 Drawing Sheets

ELASTOMERIC ARTICLES WITH IMPROVED DAMP SLIP

BACKGROUND OF THE INVENTION

Elastomeric materials have been formed into countless different articles suitable for use in many applications, such as surgical gloves, examining gloves, condoms, catheters, balloons, tubing, and the like. Elastomeric materials have been found particularly suitable for such applications due to their physical characteristics. For example, elastomeric materials, in addition to having good elastic properties, exhibit good strength characteristics and may be produced so as to be impermeable not only to aqueous solutions, but also to many solvents and oils.

Elastomeric materials are typically tacky to the touch and present a somewhat sticky surface. Tackiness of the surface of the article often renders manufacture and use of the article difficult, at best. For example articles such as gloves, catheters, or balloons may stick to formers during manufacture and to themselves and each other (commonly termed "blocking") during packaging and shipping. In addition, elastomeric articles often feel sticky to human skin. For example, elastomeric articles such as gloves may be difficult to slip over the hand during donning due to tackiness at the glove surface.

Several methods have been developed in the past for decreasing surface tack of an elastomeric article. For example, one common process has been the addition of a powder, such as talc or calcium carbonate powder, for example, to the article's surface. The powder acts as a buffer or barrier between the surface of the article and the skin to make the elastomeric article more slippery. While powder on the article surface is acceptable for some applications, powders may not be desired in certain applications, such as surgical or other clean-room type applications.

As a result, powder free coatings have been developed in an attempt to decrease surface friction of the elastomeric articles. For example, a variety of polymeric coatings have been developed for elastomeric articles in an attempt to provide the articles with increased slip at the surface. For instance, hydrophilic coatings, such as hydrophilic hydrogel polymer coatings, have been used in an attempt to increase damp donning performance.

Other processes used in the past for increasing surface slip include altering the surface of the elastomeric article itself. For example, components have been grafted to the surface of the elastomeric article in an attempt to improve slip characteristics of the article. U.S. Pat. No. 4,595,632 to Mayhan, et al., which is incorporated herein by reference thereto as to all relevant matter, discloses a process for forming elastomeric articles including a grafted fluorocarbon on the surface.

Some of these methods, while improving surface slip characteristics of elastomeric articles with respect to dry surfaces, have not similarly improved the slip characteristics of the articles with respect to damp surfaces. More specifically, when the treated surface becomes damp, the coefficient of friction increases, and the article, such as the glove, for example, becomes difficult to slip over the skin.

The damp slip characteristics of an elastomeric article may be particularly important in medical applications. For example, catheters must often have the ability to slide across damp internal epithelial tissue. Similarly, medical gloves are usually donned after the hands have been washed without complete drying, so that the hands may be quite damp while the wearer is attempting to slide the gloves over the skin.

A variety of lubricants have been developed in an attempt to alleviate the problems of damp slip characteristics in these articles. Exemplary lubricants used include, for example, silicone lubricants, surfactant lubricants, and fatty amine lubricants.

Though application of such lubricants has improved damp slip characteristics somewhat, a great deal of room for improvement still exists, and there remains a need in the art for elastomeric articles which exhibit good slip characteristics under damp conditions as well as exhibiting other characteristics desired in an elastomeric article.

SUMMARY OF THE INVENTION

In one embodiment, the present invention is directed to an elastomeric article, such as a glove, which includes a primary matrix with an elastomeric polymer at a surface. This surface of the primary matrix includes a fluorocarbon functional group grafted to the elastomeric polymer. The fluorocarbon may be grafted to the polymer backbone with an ester linkage. In addition, the article includes a silicone lubricant applied to the surface of the article having the fluorocarbon graft. In one embodiment, the lubricant may comprise a hydrophilic modified silicone. In one embodiment, the lubricant may comprise a hydrophilic amino modified silicone.

The present invention is also directed to a method for forming the elastomeric articles. In general, the method includes forming a primary matrix with an elastomeric polymer on a former. A fluorocarbon is then grafted to the polymer backbone of the elastomeric polymer with an ester linkage. A modified silicone lubricant is applied to the same surface of the article to which the fluorocarbon has been grafted. When the silicone lubricant is applied to the article surface, a bond may be formed between the modified silicone lubricant and the fluorocarbon.

BRIEF DESCRIPTION OF THE DRAWINGS

A full and enabling disclosure of the present invention, including the best mode thereof to one of ordinary skill in the art, is set forth more particularly in the remainder of the specification, including reference to the accompanying figures in which.

DETAILED DESCRIPTION OF PREFERRED EMBODIMENTS

It is to be understood by one of ordinary skill in the art that the present discussion is a description of exemplary embodiments only, and is not intended as limiting the broader aspects of the present invention, which broader aspects are embodied in the exemplary construction. Moreover, it should be further understood that even though the elastomeric articles referred to in the remainder of this description are generally referred to as gloves, the present invention is applicable to other elastomeric articles as well, and is not to be limited to gloves.

In one aspect, the present invention is directed to an elastomeric article which includes a fluorocarbon graft on a surface of the article and a lubricious coating applied to the article which, when combined with the fluorocarbon graft, may provide an elastomeric article exhibiting excellent slip characteristics when either wet or dry. The lubricious coating used in the present invention includes a modified silicone polymer which displays a synergism with the graft, providing superior damp slip characteristics to the article. Other lubricants may also be coated on the article which may physically restrict movement of the modified silicone. This may contribute to keeping the silicone polymer as well as the second lubricant on the surface of the article, thereby further improving damp slip characteristics.

The process of the present invention includes grafting a fluorocarbon onto the surface of an elastomeric article. The process is applicable to any article which contains aliphatic carbon—carbon unsaturation on the surface, but in general is directed to elastomeric articles. A fluorocarbon graft to an elastomeric article may not only improve the slip characteristics of the article, but may also improve the resistance of the article to oxidation processes, thereby improving shelf life of the article.

Any elastomeric article which includes an unsaturated polymeric matrix at the surface may be processed according to the present invention. For example, the gloves of the present invention may be formed of a natural or a synthetic latex or a dissolved elastomeric polymer, as desired. For instance, the gloves of the present invention may be formed of a natural rubber, a nitrile rubber, a polyurethane, a homopolymer of a conjugated diene, a copolymer of a least two conjugated dienes, a copolymer of at least one conjugated diene and at least one vinyl monomer, or any other suitable combinations thereof. Moreover, combinations of polymers or copolymers may be in a single layer of an article or in separate layers, such as in a multi-layer article. In such an embodiment, the only layer of the article which would require an unsaturated polymeric matrix would be that layer at the surface of the article to which the fluorocarbon will be grafted.

Figure 1:
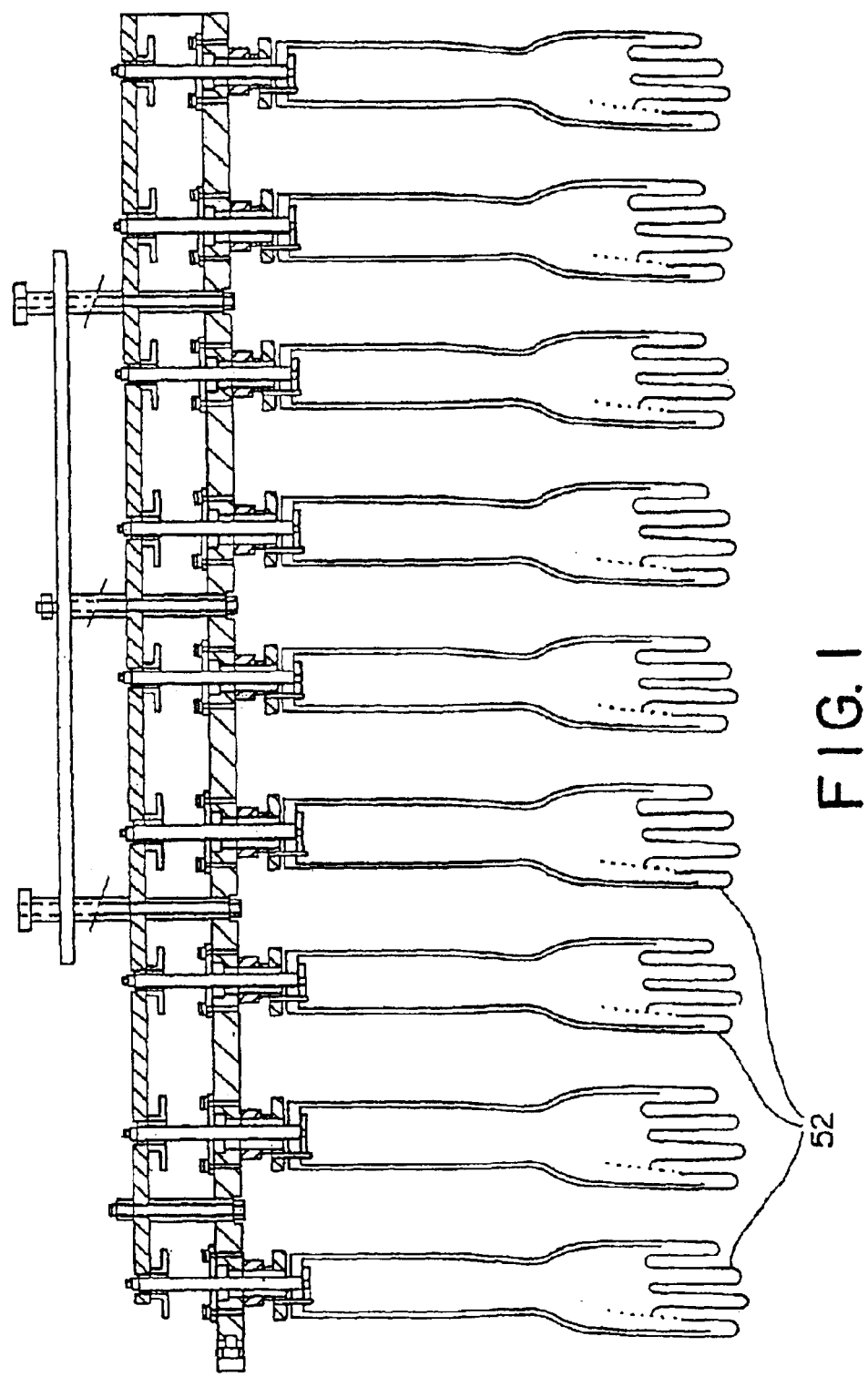
FIG. 1 is an illustration of glove-shaped formers that may be used in accordance with one embodiment of the present invention.

In general, the elastomeric articles of the present invention may be formed by any suitable process. For example, an elastomeric glove may be formed by a series of dipping processes of a former of the shape of the finished article. FIG. 1 is an illustration of a series of glove molds or formers 52 which may be used to form the gloves of the present invention. The formers 52 shown in FIG. 1 are illustrated on a pallet as is conventionally used in a batch processing operation, but it should be understood that the process of the present invention may equally be utilized in a continuous operation. A former 52 may generally be a contoured mold having a textured or smooth surface which may accept a series of coatings and release the formed article. Possible materials for the surface of former 52 may include any suitable surface material. For example, the surface of former 52 may be formed of ceramic, porcelain, glass, metal, or certain fluorocarbons.

In many applications, a former is cleaned prior to formation of a glove. The cleaning process may generally include an optional water pre-rinse followed by an acid wash. After the acid wash, the former may be rinsed with water and dipped in a heated caustic solution prior to a final water rinse. After the cleaning process, a glove may be formed on the former through a series of dipping and drying steps.

Figure 2:
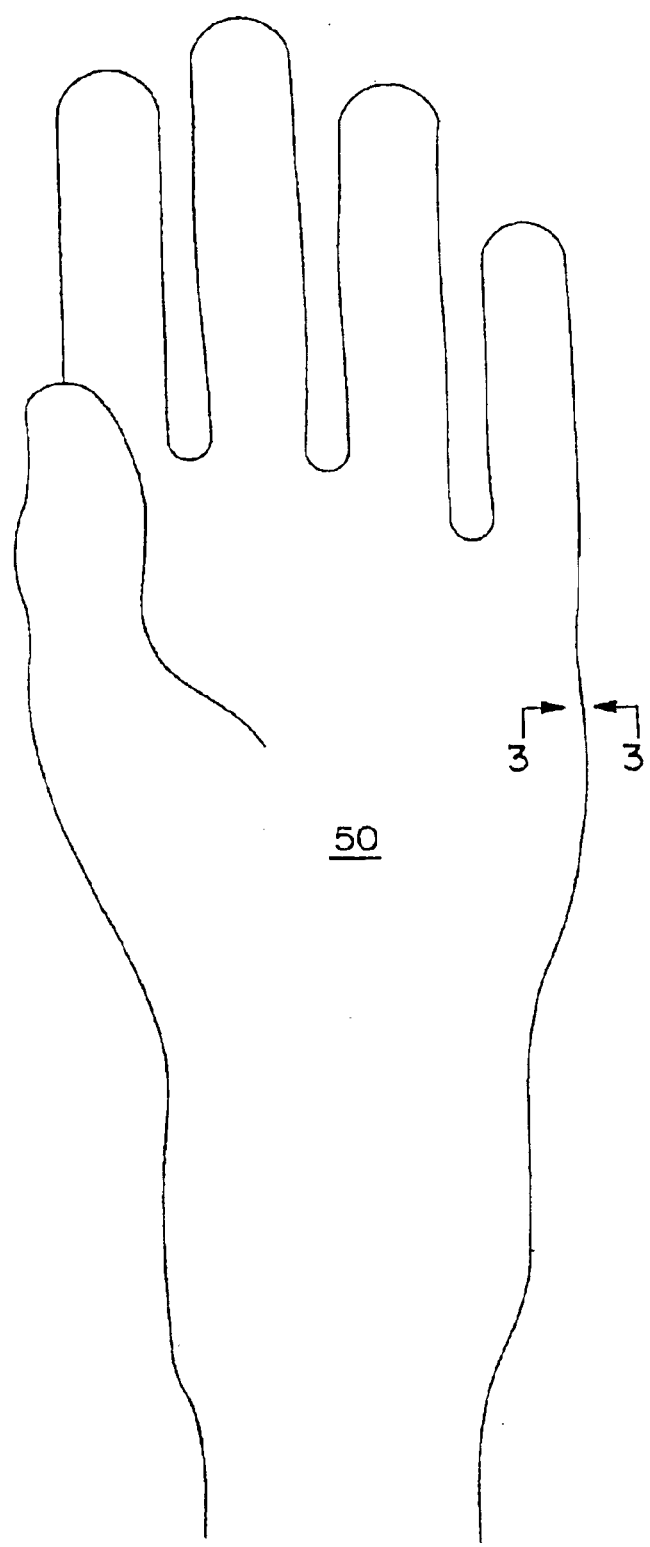
FIG. 2 is a front view of a glove according to the present invention.

FIG. 2 illustrates one possible embodiment of a glove 50 which may be formed on former 52. In one embodiment, the glove 50 may be formed through a series of dippings or immersions of the former 52. For example, in one embodiment, after cleaning, the former 52 may be dipped into a coagulant composition prior to forming the main body or primary matrix of the glove on the former. For purposes of this disclosure, the primary matrix of the glove is defined to be the main body of the glove and includes one or more layers of elastomeric material. A coagulant causes the base polymer which may form the primary matrix of the glove to coagulate. Coagulant compositions that may be used in the present invention may include powders, to ease stripping of the glove from the former, or, if desired, may be powder free. In one embodiment, a powder free coagulant composition may be used which includes water soluble salts of calcium, zinc, aluminum, and the like. For example, in one embodiment, calcium nitrate in water or alcohol may be used in the coagulant composition. In such an embodiment, calcium nitrate may be present in the solution in an amount of up to about 40% by weight. Optionally, the coagulant composition may contain other additives, such as surfactants, that improve the characteristics the glove.

After being immersed in the coagulant composition, the former may be withdrawn and the coagulant present on the surface of the former allowed to dry. For many applications, the coagulant may be air dried for a time of from about one minute to about two minutes. Once dried, a residual coating of the coagulant is left on the former.

In one embodiment, after the coagulant dip, the former may be immersed or dipped into a latex emulsion of the desired elastomeric polymer. A latex is defined for the purposes of this invention as a colloid in which the elastomeric polymer is suspended in water.

In general, a latex emulsion of the present invention may have a dry rubber content (DRC) of less than about 50% or alternatively a total solid content (TSC) of less than about 50%. In one embodiment, a latex emulsion may have a DRC or a TSC content of less than about 25%. A latex emulsion may also contain various additives such as pH adjustors, stabilizers, and the like.

Upon contact of the latex with the coagulant composition, the coagulant causes some of the latex to become locally unstable and coagulate on the surface of the former. Any additives in the coagulant composition may, depending upon what they are, form a layer between the former and the latex film, or alternatively may be incorporated into the latex film and may subsequently be removed during a leaching process. After the desired amount of time, the former is withdrawn from the latex emulsion, and the coagulated layer is allowed to coalesce fully on the former.

The amount of time the former is immersed in the emulsion (commonly termed "dwell time") determines the thickness of the film. Increasing the dwell time of the former in the latex causes the thickness of the film to increase. The total thickness of the film forming the glove body may depend on other parameters as well, including, for example, the solids content of the latex emulsion and the additive content of the latex emulsion and/or the coagulant composition.

After being dipped into the latex emulsion, the former is then heated to cure the polymer.

In one embodiment of the present invention, additional layers can be formed on the first layer, such that the primary matrix of the glove includes multiple layers. Such a process is generally termed an over-dip process. In one embodiment, an over-dip process may be carried out by immersing the former into an emulsion or a solution of the desired polymer. Additional layers of the primary matrix may enhance certain characteristics of the glove. For instance, an additional layer on the base layer of the glove may provide the aliphatic carbon—carbon unsaturation on the glove surface required in order to accept the fluorocarbon graft of the present invention.

In general, formation of one or more layers on the glove by any suitable technique may be included in the process of the present invention. In those embodiments wherein one or more over-dip processes are carried out, the desired polymer which will be located on the surface of the primary matrix of the glove should, in order to accept the fluorocarbon graft of the present invention, include an unsaturated polymeric matrix.

The elastomeric article of the present invention need not be formed from a coagulated latex emulsion. For example, in one embodiment, the elastomeric article of the present invention may be formed of one or more polymers which have been dissolved in a suitable solvent and then allowed to dry on a former in the desired shape as the solvent is evaporated from the solution. For example, one or more unsaturated block copolymers as are generally known in the art may be dissolved in a solvent, such as toluene, and may then be dried on a former in the shape of the desired elastomeric article. Suitable block copolymers include, for example, unsaturated styrene-isoprene-styrene (S—I—S) block copolymers, styrene-polybutadiene-styrene (S—B—S) block copolymers, styrene-butadiene (S—B) block copolymers, and mixtures thereof.

In one embodiment, the primary matrix of the glove may be formed of one or more layers of elastomeric polymers. For example, in one embodiment, the primary matrix of the glove may include an inner layer formed of one or more styrene-ethylene butylene-styrene (S-EB-S) block copolymers. In this embodiment, the first layer of the glove, once formed, may be subjected to an over-dip process, in order to form a second layer of elastomeric material on the glove body which may include an unsaturated polymeric matrix necessary for the fluorocarbon graft of the present invention. For example, an overcoat including one or more unsaturated block copolymers may be formed on a surface of the S-EB-S primary matrix. The unsaturated polymer surface of the overcoat can then accept the graft of the present invention. For example, in one embodiment, one or more S—I—S block copolymers, S—B—S block copolymers, S—B block copolymers, or mixtures thereof may form an overcoat on the glove which includes an S-EB-S block copolymer primary matrix.

After the primary matrix of the article is formed including any desired overcoats, a fluorocarbon grafting process is carried out. In one embodiment, the fluorocarbon graft may occur prior to curing the primary matrix. However, as the process for grafting the fluorocarbon to the polymer substrate may be the same whether the polymer is cured before or after the graft, for purposes of simplification, the following discussion is generally directed to those embodiments wherein the fluorocarbon is grafted to the surface of the elastomeric article following curing of the primary matrix. It will also be appreciated by those skilled in the art that a curing or vulcanizing step will not be necessary at all in certain embodiments of the present invention.

In one embodiment, the polymer may be cured prior to the grafting of the present invention at a temperature of between about 100° C. and about 150° C. In general, a natural or synthetic rubber latex may be vulcanized by high temperature reaction with a vulcanizing agent, generally sulfur, to cause cross-linking of the polymer chains. In addition to vulcanizing the latex, the high temperature process may cause the evaporation of any volatile components remaining on the former, such as any remaining water, for example.

The fluorocarbon grafting process involves first epoxidizing the surface of the article, followed by reacting the epoxy groups with an appropriate fluorocarbon. In one embodiment, both steps may be carried out in a single process, though this is not required by the present invention. Prior to epoxidizing the surface of the article, the article may first be cleaned and/or leached. In one embodiment, the surface may be cleaned with a solution containing either benzene or toluene combined with isopropyl alcohol.

After cleaning, the surface of the elastomeric article may be exposed to a suitable peroxy acid (i.e., a peroxycarboxylic acid) at a suitable reaction temperature in order to epoxidize the surface of the article. For example, the article may be exposed to a peroxy acid having the general formula of:

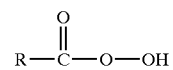

at a temperature of less than about 100° C. In one embodiment, the article may be exposed to a peroxy acid at a temperature of between about 10° C. and about 40° C. In one embodiment, the article may be exposed to a peroxy acid at ambient temperature (i.e., about 20° C.).

Upon reaction of the peroxy acid with the unsaturated polymer matrix at the surface of the glove, the surface of the glove becomes epoxidized with the formation of epoxide, or oxirane, groups at the carbon—carbon double bond sites:

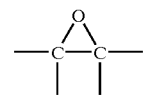

The epoxidized surface of the elastomeric article is then ready to accept a fluorocarbon graft. The epoxidized surface of the elastomeric article may be grafted by exposing the surface to a solution containing aliphatic, aromatic, or alicyclic chemical groups having one or more fluorine atoms.

In one embodiment, peroxytrifluoroacetic acid may be used as the grafting medium. This may be found desirable in some embodiments of the present invention, because the same acid solution may be used to epoxidize the surface of the substrate and provide the fluorine atoms. Therefore, epoxidation and grafting may be performed successively in the same acid bath without interruption to yield the graft. In another possible embodiment, the elastomeric article may be submersed in a solution including both trifluoroacetic acid and hydrogen peroxide, such that the epoxidation and the grafting may be performed in the same bath without interruption. For example, a solution containing between about 25% to about 50% trifluoroacetic acid by weight and between about 10% and about 25% hydrogen peroxide by weight may be used to graft the fluorocarbon to the surface of the elastomeric article. In one embodiment, the solution may contain between about 30% and about 40% trifluoroacetic acid by weight and between about 15% and about 20% hydrogen peroxide by weight.

The grafting solution need not be aqueous. Any suitable solvent capable of dissolving the fluorocarbon grafting agent without either impairing the substrate or reacting with the fluorocarbon grafting agent may be used. For example, one embodiment includes the use of isopropyl alcohol as a solvent.

As the grafting reaction proceeds, the hydroxy ester tends to esterify to the diester and also to hydrolyze to the dihydroxy, as indicated below:

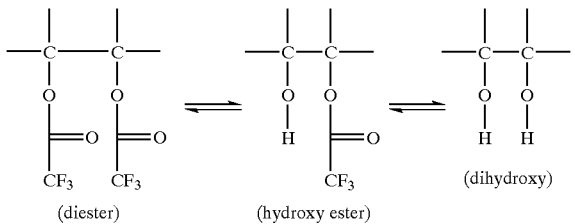

It has been found that the diester is hydrolytically unstable but that the hydroxy ester exhibits a high level of hydrolytic stability. This is believed to be due to an intramolecular hydrogen bond between the adjacent hydroxy group and the ester linkage. In one embodiment, conversion of the diester to the more hydrolytically stable hydroxy ester may be accomplished by the further step of placing the fluorocarbon grafted article in an aqueous solution maintained at a pH of about 8 to about 11. In one embodiment, the fluorocarbon grafted article may be placed in an aqueous solution maintained at a pH of between about 9 and about 11. For example, the article may be placed in a potassium hydroxide solution at a pH of between about 9 and about 10. This reaction may proceed at room temperature and, depending on substrate composition and graft depth, the dwell time of the substrate in the alkaline solution may generally fall within the range of about 1 to about 3 hours.

Although peroxytrifluoroacetic acid has been found effective as a grafting agent (and also as an epoxidizing agent), a variety of agents other than fluorocarboxylic acids may be used to graft fluorocarbon groups onto the epoxidized surface of a preformed substrate. Such agents include, for example, fluorine-containing acetals, acetoacetates, acetonitriles, acetylenes, acid anhydrides, acyl halides, alcohols, aldehydes, alkyl halides, alkyl hydroperoxides, amides, amines (primary, secondary, or tertiary), azides, cyanates, ketones, malonates, organomagnesium halides, phenols, phosphines, and phthalimides.

Although the thermodynamic feasibility of all of these reactions is clear, it will be understood that the reaction conditions and solvents will vary depending upon the particular substrate and grafting material selected.

In one embodiment, the grafting process may continue until substantially all of the reactive sites on the substrate surface (i.e., all of the sites of unsaturation) are occupied by the fluorocarbon graft. The resulting article may have both the properties of the elastomeric polymer forming the main body of the article and the surface properties of the fluorocarbon graft. In the case of an article formed from an elastomer such as natural rubber latex, the article may retain the original resilience and elasticity, but its treated surface may take on the dry slip characteristics and resistance to oxidation of the fluorocarbon. In addition to markedly increasing lubricity and ozone resistance, the fluorocarbon graft reduces the gas permeability of an elastomeric film or sheet, indicating that sub-microscopic pinholes and fissures may be sealed by the dense fluorocarbon graft. Also, to the extent that reactive sites that would otherwise be present on the surface of the substrate are occupied by the fluorocarbon graft, biocompatability is believed to be enhanced.

Once the glove surface has been grafted with the fluorocarbon, the glove may be rinsed, such as with a water rinse, and dried prior to application of the silicone lubricant of the present invention. If the fluorocarbon has been grafted onto the surface of the elastomeric article prior to curing of the elastomeric layer, the polymer may be cured after the grafting process and prior to application of the lubricant.

In one embodiment, the silicone lubricant may be applied to the glove surface while the glove is still on the former. Alternatively, the glove may be stripped prior to application of the silicone lubricant In general, the lubricant of the present invention may be a silicone-based lubricant which may provide good damp slip characteristics. In addition, the silicone lubricant of the present invention may also display polar functionality. More specifically, the lubricant of the present invention may be a modified siloxane lubricant which displays polar functionality at the dominant component on the backbone of the polymer. In one embodiment, the polar functional group on the siloxane backbone may be an amino moiety. Though not wishing to be bound by any particular theory, it is believed that a polar functional group on the siloxane polymer, such as an amino group, for example, may be attracted to the fluorocarbon ester linkage on the glove surface. It is further believed that a strong charge attraction may develop between the fluorocarbon ester linkage and the polar group on the siloxane polymer at the fluoroester linkage leading to a polar bond developing between the siloxane lubricant and the surface of the primary matrix, preventing penetration of the silicone lubricant to the interior of the glove, and improving damp slip characteristics of the glove.

As such, the polar modified siloxane lubricant and the fluorocarbon grafted polymer of the primary matrix of the glove may display a synergism, improving slip characteristics, particularly damp slip characteristics, of the elastomeric article beyond that obtained by use of either component alone or of either component used with other coatings and lubricants known in the art.

In one embodiment, the modified silicone may be an amino-modified silicone. An amino-modified silicone may be formed from an organo-modified silicone. Organo-modified polysiloxane copolymers (i.e., organo-modified silicones) and methods of making the same are generally known to those skilled in the art. Such copolymers often contain hydroxyl groups.

Amino-modification of a silicone may be performed by first substituting a halide for the hydroxyl group on the organo modified polysiloxane. The halide may then be reacted with ammonia or an amine to substitute an amino group for the halide. This latter process is called ammonolysis of halides. Alternatively, amino-modified polysiloxanes (i.e., amino-modified silicones) may be prepared according to U.S. Pat. No. 3,905,823 to Piskoti, which is hereby incorporated by reference as to all relevant material. According to Piskoti, the amino-modified polysiloxanes are prepared by mixing an organo-modified siloxane with amino-functional silanes or siloxanes and thereafter equilibrating the mixture in the presence of a base catalyst, e.g., alkali metal hydroxides, alkoxides, hydrides, alkyls, alkenyls and aryls, and silanoates.

In one embodiment, an amino modified polysiloxane may be used such as that found in a softener sold by the Dow Corning Corporation designated as DC 8600. In one embodiment the modified silicone polymer may be used in the present invention in the form of a solution or emulsion, such as an aqueous composition containing between about 0.05% by weight and about 5% by weight of the modified siloxane.

In one embodiment, the damp slip characteristics of the elastomeric article may be even further improved with the further application of a suitable lubricant to the glove surface. For example, a lubricant containing one or more high molecular weight alcohols (i.e., fatty alcohols) may be used. In one embodiment, a lubricant including hexadecanol and octadecanol and sold under the brand name Varisoft® BTMS available from the Goldschmidt Chemical Corporation may be used.

Fatty alcohols, which are defined for purposes of this disclosure as an alcohol including a straight chain of at least ten carbons, are believed to be beneficial to the slip characteristics in the gloves of the present invention because they include a slightly polar hydroxyl portion which may form a weak bond with the ester linkage of the fluorocarbon graft on the elastomeric polymer. In addition to the hydroxyl, however, they also include a long hydrocarbon tail. As previously discussed, the silicone polymer may be bonded to the surface of the glove at the fluoroester linkage. The additional weak bond between the fluoroester linkage and the fatty alcohol may bring the silicone polymer and the fatty alcohol in close proximity, leading to physical entanglement between the long hydrocarbon tail of the fatty alcohol and the silicone polymer. This may further restrict the motion of the both the silicone polymer and the lubricant, keeping both even more surface limited and further enhancing the damp donning characteristics of the glove.

Long chain lubricants such as fatty alcohols may be applied to the glove surface by any suitable method. For example, after application of the siloxane lubricant, the glove may be dipped in a solution including the desired fatty alcohols. Alternatively, a solution may be sprayed or painted on to the surface, either before or after the article is stripped from the former. In one possible embodiment, fatty alcohols may be included in solution with the modified siloxane. For example, in one embodiment, the glove may be dipped in a solution including between about 0.05 wt % and about 5 wt % amino modified silicone polymer and between about 0.02 wt % and about 5 wt % fatty alcohols. In one embodiment, the glove can be dipped in a solution or emulsion including between about 0.1 wt % and about 1 wt % amino modified silicone polymer and between about 0.1 wt % and about 1 wt % one or more fatty alcohols.

Other desired components as are generally known in the art may also be included in the solution. For example, siloxane polyethers may also be included in the solution to further enhance glove characteristics. A combination of multiple application methods is also contemplated by the present invention.

The specific process for applying a silicone lubricant to the fluorocarbon grafted surface of the elastomeric substrate depends on process characteristics. For example, variations in the process are envisioned due to the nature of the substrate, whether the article is formed by dipping a form into an elastomeric polymer latex or into a solution of the elastomeric polymer in a solvent, and the like. Methods for making the elastomeric substrate of the articles of the present invention are well known in the art.

For example, when the primary matrix is formed from compounded natural rubber latex, the latex on the former may be beaded and leached in the normal way and may then be dried and vulcanized followed by the fluorocarbon graft on the surface of the article. As previously mentioned, however, the graft may be carried out either before or after the primary matrix is cured. In one embodiment, the silicone lubricant may be applied by dipping the grafted article into an aqueous solution including both the siloxane lubricant and one or more fatty alcohols. In an alternative embodiment, the glove may be contacted with the silicone lubricant after the glove is stripped from the former. After application of the silicone lubricant and, when desired, other treatments such as application of one or more fatty alcohols, the glove may be finally dried, such as by tumble drying as is generally known in the art.

Figure 4:
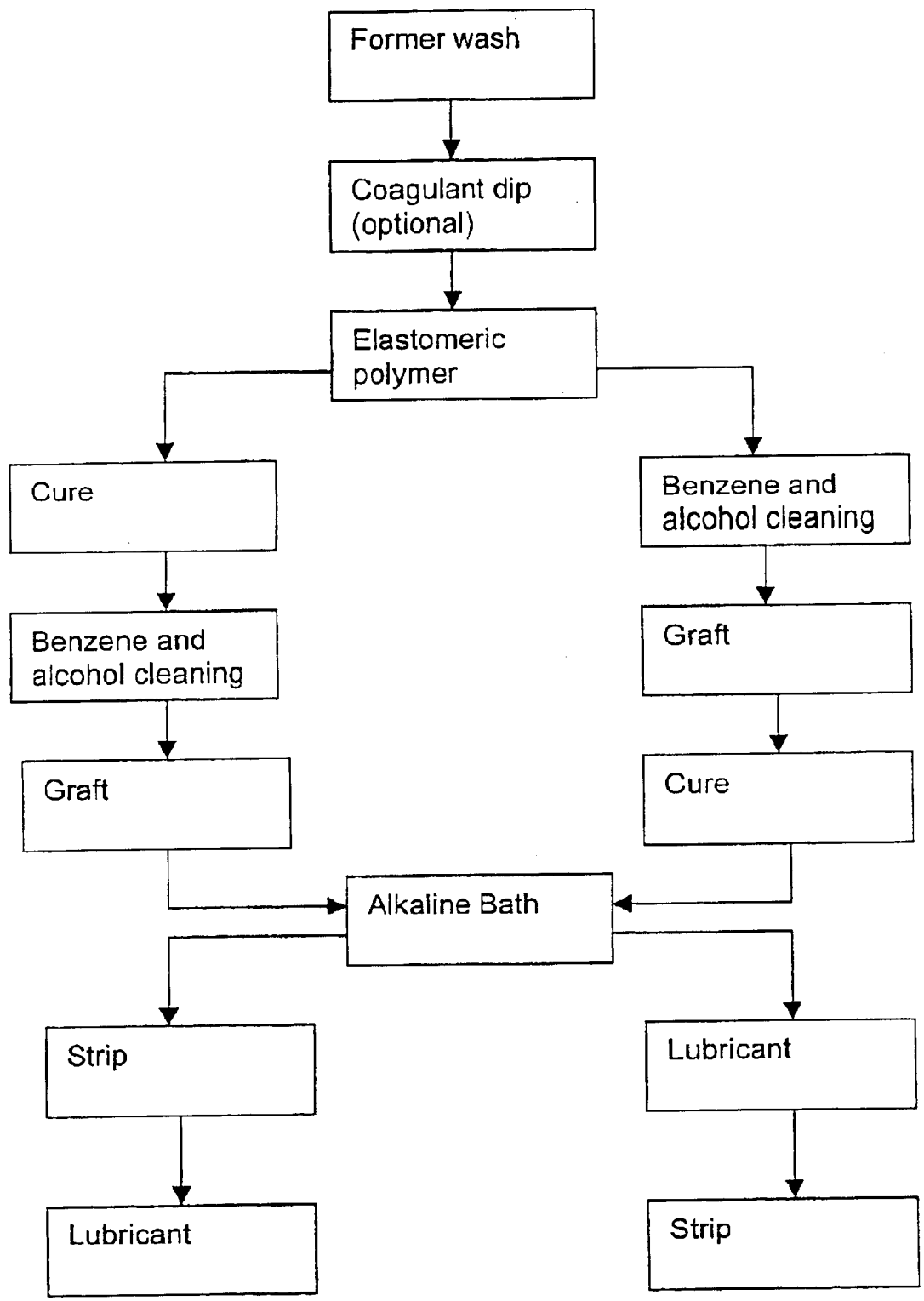
FIG. 4 is a flow diagram of one embodiment of the process of the present invention.

FIG. 4 illustrates flow diagrams for possible embodiments of the present invention. In general, the process may begin with a washing step, in which a former 52, as illustrated in FIG. 1, may be washed prior to formation of the glove on the former. Optionally, and depending at least in part on the elastomer which will form the primary matrix of the glove, the former may be coated with a coagulant composition. Once the former is prepared, the primary matrix of the glove may be formed by one or more dip-coatings into the desired elastomeric polymer composition(s). After the primary matrix of the glove has been formed, the process may continue by curing the primary matrix, cleaning the surface of the primary matrix with a benzene (or toluene) and isopropyl alcohol solution, and grafting the desired fluorocarbon moiety to the primary matrix. Alternatively, the fluorocarbon grafting process can be carried out after cleaning the surface of the primary matrix, and prior to the curing process. After the desired fluorocarbon moiety has been grafted to the article, the article may be placed in an alkaline bath for a period of time, so as to convert the fluorocarbon diester to the more hydrolytically stable hydroxy ester. After the optional alkaline bath, a lubricant including the modified silicone of the present invention may be applied to the surface of the glove, either before or after stripping the glove from the former.

In other embodiments, the elastomeric articles of the present invention may be formed according to similar methods. For example, elastomeric articles formed of polymers in dispersed, e.g., latex, form, such as, for instance polyurethanes and nitrile latex emulsions as well as articles formed of dissolved polymers, may be treated similarly to the above described method, although a vulcanizing step will not be needed in every case, as may be readily appreciated by those skilled in the art.

Figure 3:
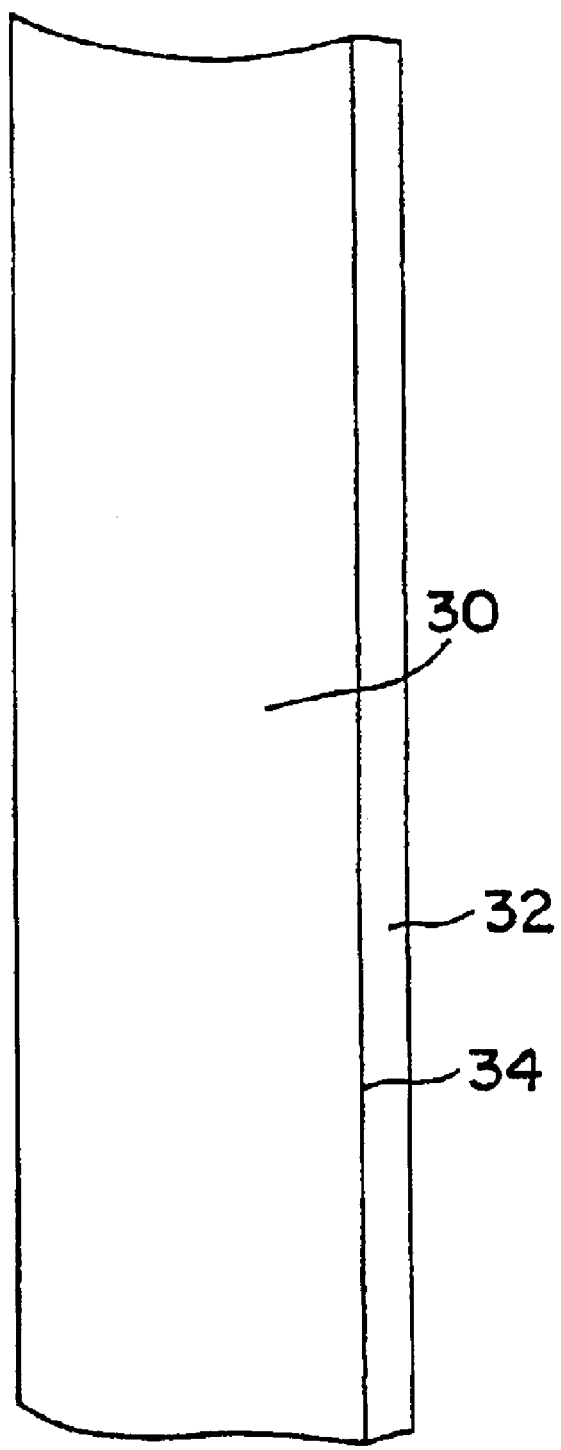
FIG. 3 is an enlarged cross-sectional view of one embodiment of an elastomeric article of the present invention.

FIG. 3 is an illustration of a cross section of a portion of one embodiment of an article made according to the present invention. In this particular embodiment, the primary matrix 30 of the glove, is a single layer primary matrix. The fluorocarbon graft 34 is at the surface of the primary matrix and the silicone lubricant 32 is applied to the surface of the primary matrix which includes the fluorocarbon graft.

Due to the synergistic relationship which develops between the fluorocarbon graft 34 at the surface of the primary matrix 30 and the silicone lubricant 32, the articles, e.g., gloves, of the present invention may have good slip characteristics, including both wet and dry slip characteristics, with no halogenation process, i.e., chlorination, necessary. Moreover, in those embodiments where no powder is applied to the former prior to formation of the primary matrix layer of the glove, the gloves produced may be powder free gloves with no powder removal processes required, as may be preferred in some applications.

The present invention may be better understood by reference to the following example, which is provided by way of explanation of the invention, not as a limitation of the invention. In fact, it will be apparent to those skilled in the art that various modifications and variations may be made of this invention without departing from the scope or spirit of the invention.

EXAMPLE

Natural latex gloves were formed by dip-coating a coagulant including calcium carbonate on a glove shaped former.

After the coagulant was on the former, a natural latex layer was formed over the coagulant layer by dip-coating. Then, the natural latex article was leached, and the latex was cured/vulcanized to form the natural latex glove on the former.

While still on the formers, the gloves were then submersed in an aqueous solution including 1,200 g trifluoroacetic acid and 2,000 g 30% hydrogen peroxide.

The gloves were removed from the solution, rinsed in water, and placed in a potassium hydroxide/water solution of pH 9.5 for 2 hours. After this time, the gloves were rinsed in water and dried.

One of the gloves was then submersed in a lubricant composition including:
- 0.5% Varisoft® BTMS (BTMS with blend of two alcohols obtained from the Goldschmidt Chemical Corporation)
- 0.45% DC 8600 (amino-modified siloxane, fatty alcohol and polyether siloxane available from the Dow Corning Corporation)
- 99.05% water The glove was then stripped from the former and tumble dried.

Another of the prepared gloves was submersed in a lubricant composition of a different siloxane lubricant, SM2140, available from the General Electric Corporation, which includes methyl groups on the polymer backbone. After submersion, this glove was stripped from the former and tumble dried.

Damp donning was then compared for the two gloves by a trained evaluator.

The glove which was coated with SM2140 was found to be donnable with damp hands, but with a great deal of difficulty. The glove was given a damp donnability rating of 3.5 according to a subjective rating scale of 1–5 which is described below in Table 1.

TABLE 1

| Rating | Description | Detail |
| --- | --- | --- |
| 5 | Excellent | Easy to don with no adjustment |
| 4 | Good | Glove donned with minimal adjustment |
| 3 | Fair | Can don with reasonable fit and some adjustment |
| 2 | Poor | Can don the glove only partially |
| 1 | Fail | Cannot don |
| 0 | Not scored | Cannot even attempt to don |

The glove coated with the other above-described composition was successfully donnable with damp hands and was given a donnability rating of 4+.

The combination of the fluorocarbon graft, the amino functionalized siloxane, and the fatty alcohol surfactant produced a glove with improved damp slip characteristics as well as good dry slip characteristics and improved resistance to oxidation. In addition, the glove prepared according to the processes of the present invention may have a whiter appearance when compared to other gloves generally known in the art.

These and other modifications and variations to the present invention may be practiced by those of ordinary skill in the art, without departing from the spirit and scope of the present invention, which is more particularly set forth in the appended claims. Furthermore, those of ordinary skill in the art will appreciate that the foregoing description is by way of example only, and is not intended to limit the invention so further described in such appended claims.

What is claimed is:

1. An elastomeric article comprising:
    a primary matrix comprising an elastomeric polymer at a first surface the elastomeric polymer initially containing epoxide groups at the surface;
    a fluorocarbon moiety grafted to the first surface, wherein said fluorocarbon moiety is grafted to the elastomeric polymer via an ester linkage formed by reaction with the epoxide group; and
    a silicone lubricant applied to the first surface, the silicone lubricant comprising a modified silicone displaying polar functionality.

2. The elastomeric article of claim 1, further comprising a long chain alcohol applied to the first surface.

3. The elastomeric article of claim 2, wherein the alcohol is selected from the group consisting of hexadecanol, octadecanol, and mixtures thereof.

4. The elastomeric article of claim 1, wherein the elastomeric polymer is a natural or synthetic rubber.

5. The elastomeric article of claim 1, wherein the elastomeric polymer is a block copolymer.

6. The elastomeric article of claim 5, wherein the block copolymer is selected from the group consisting of styrene-isoprene-styrene block copolymers, styrene-polybutadiene-styrene block copolymers, styrene-butadiene block copolymers, and mixtures thereof.

7. The elastomeric article of claim 1, wherein the primary matrix comprises an inner layer comprising an elastomeric polymer and an outer layer comprising a second elastomeric polymer, wherein the outer layer comprises the first surface of the primary matrix.

8. The elastomeric article of claim 7, wherein the inner layer comprises a styrene-ethylene butylene-styrene block copolymer.

9. The elastomeric article of claim 1, further comprising hydroxy moieties pendant to the elastomeric polymer, wherein a single hydroxy moiety and a single fluorocarbon moiety are pendant to successive carbon atoms on the elastomeric polymer.

10. The elastomeric article of claim 1, wherein the silicone is amino-modified.

11. The elastomeric article of claim 1, wherein the fluorocarbon moieties are bonded to the silicone.

12. The elastomeric article of claim 1, wherein the elastomeric article is a glove.

13. The elastomeric article of claim 12, wherein the donning side of the glove is the first surface.

14. The elastomeric article of claim 12, wherein the glove is a powder free glove.

15. An elastomeric glove comprising:
    a primary matrix comprising an elastomeric polymer at a first surface, the elastomeric polymer initially containing epoxide groups at the surface, wherein the first surface is a donning side;
    a fluorocarbon moiety grafted to the elastomeric polymer with an ester linkage formed by reaction with the epoxide groups; and
    a silicone lubricant applied to the donning side, the silicone lubricant comprising an amino-modified silicone.

16. The elastomeric glove of claim 15, further comprising a long chain alcohol applied to the donning side.

17. The elastomeric glove of claim 16, wherein the alcohol is selected from the group consisting of hexadecanol, octadecanol, and a mixture thereof.

18. The elastomeric glove of claim 15, further comprising hydroxy moieties pendant to the elastomeric polymer, wherein a single hydroxy moiety and a single fluorocarbon moiety are pendant to successive carbon atoms on the elastomeric polymer.

19. The elastomeric glove of claim 15, wherein the elastomeric polymer is a natural or a synthetic rubber.

20. The elastomeric glove of claim 15, wherein the elastomeric polymer is a block copolymer.

21. The elastomeric glove of claim 20, wherein the block copolymer is selected from the group consisting of styrene-isoprene-styrene block copolymers, styrene-polybutadiene-styrene block copolymers, styrene-butadiene block copolymers, and mixtures thereof.

22. The elastomeric glove of claim 15, wherein the primary matrix comprises an inner layer of an elastomeric polymer and an outer layer of an elastomeric polymer, wherein the outer layer is the first surface of the primary matrix.

23. The elastomeric glove of claim 22, wherein the inner layer comprises a styrene-ethylene butylene-styrene block copolymer.

24. The elastomeric article of claim 15, wherein the glove is a powder free glove.

25. A process for forming an elastomeric article comprising:
   forming a primary matrix on a former, the primary matrix comprising an unsaturated elastomeric polymer located on a first surface, the polymer containing epoxide groups;
   grafting a fluorocarbon moiety to the elastomeric polymer with an ester linkage by reaction with the epoxide groups;
   applying modified silicone which displays polar functionality to the first surface, thereby forming the article; and
   stripping the article from the former.

26. The process of claim 25, further comprising curing the elastomeric polymer on the former.

27. The process of claim 26, wherein the elastomeric polymer is cured prior to grafting the fluorocarbon to the elastomeric polymer.

28. The process of claim 26, wherein the elastomeric polymer is cured after grafting the fluorocarbon to the elastomeric polymer.

29. The process of claim 25, wherein the article is stripped from the former prior to application of the modified silicone.

30. The process of claim 25, wherein the article is stripped from the former after application of the modified silicone.

31. The process of claim 25, further comprising applying a long chain alcohol to the first surface.

32. The process of claim 31, comprising applying a solution of less than about 5% by weight of the long chain alcohol.

33. The process of claim 25, further comprising applying a solution of between about 0.05% and about 5% by weight of the modified silicone.

34. The process of claim 25, wherein the elastomeric article is a glove.

35. The process of claim 34, wherein the donning side of the glove is the first surface.

36. The process of claim 25, wherein the modified silicone is amino-modified.

37. The process of claim 25, further comprising submersing the primary matrix on the former in an aqueous solution at a pH of between about 8 and about 11 for a p nod of between about 1 and about 3 hours after grafting the fluorocarbon moiety to the elastomeric polymer.

38. The process of claim 25, wherein the elastomeric polymer is a natural or a synthetic rubber.

39. The process of claim 25, wherein the elastomeric polymer is a block copolymer.

40. The process of claim 25, wherein the primary matrix comprises an inner layer and an outer layer, wherein the inner layer comprises a styrene-ethylene butylene-styrene block copolymer and the outer layer comprises the unsaturated elastomeric polymer.

41. An elastomeric glove comprising:
   a primary matrix comprising an elastomeric polymer at a first surface the elastomeric polymer initially containing epoxide groups at the surface, wherein the first surface is a donning side;
   a fluorocarbon moiety grafted to the elastomeric polymer with an ester linkage formed by reaction with the epoxide groups; and
   a lubricant composition comprising a silicone and a long chain alcohol applied to the donning side.

* * * * *

UNITED STATES PATENT AND TRADEMARK OFFICE
CERTIFICATE OF CORRECTION

PATENT NO. : 6,805,963 B2
DATED : October 19, 2004
INVENTOR(S) : Janssen et al.

It is certified that error appears in the above-identified patent and that said Letters Patent is hereby corrected as shown below:

Column 12,
Line 9, the word "group" should be -- groups --.

Column 14,
Line 20, the word "p nod" should be -- period --.

Signed and Sealed this

Thirtieth Day of August, 2005

JON W. DUDAS
*Director of the United States Patent and Trademark Office*